(12) United States Patent
Tsaur et al.

(10) Patent No.: US 7,659,235 B2
(45) Date of Patent: *Feb. 9, 2010

(54) STABLE LIQUID CLEANSING COMPOSITIONS WHICH MAY BE PREPARED USING FATTY ACYL ISETHIONATE SURFACTANTS

(75) Inventors: Liang Sheng Tsaur, Norwood, NJ (US); Kavssery Parameswaran Ananthapadmanabhan, Woodbury, NJ (US); Virgilio Barba Villa, Emerson, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 90 days.

This patent is subject to a terminal disclaimer.

(21) Appl. No.: 11/613,617

(22) Filed: Dec. 20, 2006

(65) Prior Publication Data

US 2008/0153729 A1    Jun. 26, 2008

(51) Int. Cl.
*A61K 7/00*    (2006.01)
(52) U.S. Cl. .............. 510/130; 510/159; 510/425; 510/426; 510/501; 510/491
(58) Field of Classification Search .............. None
See application file for complete search history.

(56) References Cited

U.S. PATENT DOCUMENTS

| | | |
|---|---|---|
| 3,723,325 A | 3/1973 | Parran, Jr. |
| 4,565,647 A | 1/1986 | Llenado |
| 5,009,814 A | 4/1991 | Kelkenberg et al. |
| 5,132,037 A | 7/1992 | Greene et al. |
| 5,234,619 A | 8/1993 | Greene et al. |
| 5,290,471 A | 3/1994 | Greene et al. |
| 5,372,751 A | 12/1994 | Rys-Cicciari et al. |
| 5,389,279 A | 2/1995 | Au et al. |
| 5,415,810 A | 5/1995 | Lee et al. |
| 5,739,365 A | 4/1998 | Briody et al. |
| 5,952,286 A | 9/1999 | Puvvada et al. |
| 6,077,816 A | 6/2000 | Puvvada et al. |
| 2004/0224863 A1 | 11/2004 | Sun et al. |

FOREIGN PATENT DOCUMENTS

| | | |
|---|---|---|
| EP | 1 479 365 | 11/2004 |
| EP | 1479365 | 11/2004 |
| WO | 97/05857 | 2/1997 |
| WO | WO 97/05857 | 2/1997 |
| WO | 99/32069 | 7/1999 |
| WO | WO 99/32069 | 7/1999 |

(Continued)

OTHER PUBLICATIONS

Co-pending application: Tsaur et al.; U.S. Appl. No. 11/613,696, filed Dec. 20, 2006.

(Continued)

*Primary Examiner*—Necholus Ogden, Jr.
(74) *Attorney, Agent, or Firm*—Ronald A. Koatz

(57) ABSTRACT

The invention provides liquid cleanser compositions which can use fatty acyl isethionates mixtures, regardless of free fatty acid content of isethionates mixture or chain length distribution of isethionates mixture. The key is to ensure a specific combination of liquid crystal inducer (of surfactant phase) and of modifier so that the isethionates will be stable at low and high temperatures.

6 Claims, 4 Drawing Sheets

FOREIGN PATENT DOCUMENTS

| WO | 00/21492 | 4/2000 |
| --- | --- | --- |
| WO | 03/017968 | 3/2003 |
| WO | WO 03/017968 | 3/2003 |
| WO | 2008/074617 A | 6/2008 |

OTHER PUBLICATIONS

Co-pending application: Tsaur et al.; U.S. Appl. No. 11/613,666, filed Dec. 20, 2006.

XP-002474464, Oct. 11, 1988, English abstract of JP19870077976 (based on JP63243200).

PCT Search Report International application No. PCT/EP2007/063128 mailed Apr. 15, 2008.

XP-002474464, Oct. 1988, English abstract of JP 1987-0077976 (based on JP 63-243200).

Co-pending application: Tsaur; U.S. Appl. No. 11/850,159, filed Sep. 5, 2007.

Co-pending application: Tsaur; U.S. Appl. No. 11/958,471, filed Dec. 18, 2007.

International Search Report on Application No. PCT/EP2008/060835 dated Jan. 26, 2009 (equivalent to related U.S. Appl. No. 11/850,159).

International Preliminary Examination Report on Application No. PCT/EP2007/063128.

Co-pending application for: Applicant: Tsaur et al.; U.S. Appl. No. 12/235,955, filed Sep. 23, 2008, entitled Stable Cleansing Compositions Containing Fatty Acyl Isethionate Surfactant Products Having More Than 10 wt. % of Fatty Acid/Fatty Soap Content Using High Level of Polyol and Methods Thereof.

STABLE LIQUID CLEANSING COMPOSITIONS WHICH MAY BE PREPARED USING FATTY ACYL ISETHIONATE SURFACTANTS

FIELD OF THE INVENTION

The invention is directed to personal care skin or hair liquid cleansing compositions. In particular, it relates to such personal care skin or hair cleansing compositions comprising fatty acyl isethionate surfactants. Such commercially available surfactant products comprise a mixture of fatty acyl isethionates and free fatty acid, although no free fatty acid may be present. The compositions of the invention are stable regardless of what type of fatty acyl isethionates is used.

BACKGROUND OF THE INVENTION

Fatty acyl isethionates (e.g., cocoyl isethionates) are anionic surfactants highly desirable in personal care skin or hair cleansing products, particularly in personal care products, because they lather well, are mild to the skin and have good emollient properties. Typically, fatty acid isethionates are produced by esterification of fatty acids or by reaction of fatty acid chloride having carbon chain length of $C_8$ to $C_{20}$ with isethionate. A typical surfactant product containing fatty acyl isethionate contains about 45 to 95 wt. % fatty acyl isethionates and 0 to 40 wt. % free fatty acid, in addition to isethionates salts, typically at less than 5%, and trace (less than 2 wt. %) of other impurities.

A persistent problem with the ready use of fatty acyl isethionates in liquid compositions, however, has been the low solubility of these compounds in water. This is especially true for fatty acyl isethionate surfactant products containing high level of free fatty acid (10% by wt. or higher) and/or long chain fatty acyl isethionates (e.g., $C_{14}$ and higher). The fatty acyl isethionate component tends to form insoluble surfactant crystals with the amount of crystals depending strongly on the storage temperature due to the wide range of dissolution temperatures of these crystals. This in turn may result in unstable liquid cleansers which exhibit very thick or very thin consistency at low and elevated temperatures.

It would therefore be of tremendous advantage to have compositions having consistent viscosity; as well as a way of manipulating compositional ingredients to ensure such consistent viscosity is obtained and that fatty acyl isethionate product, no matter what their free fatty acid content or their chain lengths, can be readily used. The present invention provides precisely such compositions and processes for making such compositions.

Specifically, the invention recognizes that the problem of inconsistent viscosity can be resolved by converting part or all of the fatty acyl isethionate surfactant crystals to surfactant liquid crystals wherein the liquid crystals occupy sufficient phase volume to ensure stability, said stability being defined by the absence of visible physical separation after two weeks of storage at 40° C. This is accomplished by using a specific combination of liquid crystal modifiers (e.g., fatty acids, fatty alcohols); and sufficiently high levels of a surfactant liquid crystal inducer (e.g., alkanolamide, alkylamineoxide) as a percent of total fatty acyl isethionate plus synthetic surfactant. The specific combination of liquid crystal inducer and liquid crystal modifier creates a consistent viscosity which allows fatty acyl isethionates product, regardless of free fatty acid content or chain length of isethionates, to be storage stable.

Acyl isethionate liquids do exist in the art. U.S. Pat. No. 5,415,810 to Lee et al., for example, discloses compositions comprising fatty acyl isethionates and zwitterionic surfactant (e.g., cocoamidopropyl betaines), presumably to help solubilize the isethionate and make an isotropic liquid. The reference separately teaches away from use of both alkanolamides (column 1, lines 27-30), and use of free fatty acids, especially longer chain fatty acids (column 2, lines 34-39), let alone the use of both specifically in combination.

U.S. Pat. No. 5,739,365 to Brody et al. and U.S. Publication U.S. 2004/0224863 both disclose use of ammonium counterion to help solubilize fatty acid isethionate.

U.S. Pat. No. 5,132,037 to Greene et al. (and related U.S. Pat. No. 5,234,619 and U.S. Pat. No. 5,290,471) disclose compositions with $C_8$ to $C_{22}$ acyl isethionates, synthetics, and free fatty acid, preferably $C_{16}$ or higher. The liquid crystal inducers (e.g., alkanolamide) of the subject invention are not disclosed, nor is a process to use both liquid crystal modifiers and liquid crystal inducers specifically together to provide long term stability of acyl isethionates.

U.S. Pat. Nos. 5,952,286 and 6,077,816, both to Puvvada, disclose liquid cleansing compositions which may contain acyl isethionates and which comprise soluble, lamellar phase inducing structurant (e.g., branched fatty acid). While amides may be optionally used in a long recitation of optional ingredients, there is no teaching or disclosure that they need be used; that they must be used in combination with liquid crystal modifier to consistently enhance stability of acyl isethionate; let alone that they must be used in certain minimal amounts. It is noted that the lamellar inducing structurants claimed in the Puvvada patents are branched fatty acids or branched fatty alcohols such as isostearic acid or isostearic alcohol. According to the subject invention straight chain fatty acids and/or straight chain fatty alcohols must form the predominant amount of fatty acid and/or alcohol (e.g., modifier) which are used in combination with alkanolamide. In fact, branched liquid fatty acid and/or branched fatty alcohol are not required at all in the subject invention. If used, however, the amount should be limited to no more than 30 wt %, preferably no more than 20 wt %, even more preferably 10% or less of total fatty acids and/or fatty alcohols in the liquid composition of the invention.

None of the references, alone or together, teach or suggest compositions comprising acyl isethionate where acyl isethionate/fatty acid crystals are converted in part, or completely, to a surfactant liquid crystal using specific combinations of high levels of liquid crystal inducer (e.g., alkanolamide) and liquid crystal modifier (e.g., predominantly straight chain fatty acid) in order to provide acyl isethionate containing liquids, regardless of the fatty acid content or fatty acid chain length of the acyl isethionates surfactant; which compositions have a product viscosity less sensitive to temperature, and which compositions are stable at both low and elevated temperature storage conditions.

BRIEF SUMMARY OF THE INVENTION

In one embodiment, the present invention relates to novel liquid cleansing compositions which are formed by combination of (a) surfactant liquid crystal inducers, which helps formation of liquid crystals rather than solid crystals; and (b) liquid crystal modifier.

More specifically, the invention comprises liquid cleansing compositions comprising:

(a) 1 to 30%, preferably 3 to 25% by wt. fatty acyl isethionates (fatty acid salts and free fatty acids are not counted here but as part of component (d) below);

(b) 1 to 30%, preferably 3% to 25% by wt. of a co-surfactant selected from the group consisting of anionic surfactants, nonionic surfactants, amphoteric surfactants, zwitterionic surfactants, and mixtures thereof;

(c) 0.5 to 10%, preferably 1.0 to 8% by wt. of a surfactant liquid crystal inducer which, when added in liquid crystal inducing amount, ensures that a liquid cleanser composition comprising (a) and (b) forms a liquid crystal phase at typical storage conditions;

said liquid crystal inducer used at a level of ≧10%, preferably ≧15%, more preferably ≧20% by wt. of the total amount of fatty isethionate (a) and co-surfactant (b) combined;

(d) 0.5 to 14% of a liquid crystal modifier selected from the group consisting of straight chain fatty acids; or a mixture of straight chain fatty acids with straight chain fatty alcohols and/or aliphatic hydrocarbon oils (i.e., straight chain acids must be used and they may be used alone or in combination with the alcohols and/or hydrocarbon oils); The liquid crystal modifier is used at a level of at least 10%, preferably 20 wt % of fatty acyl isethionates (a) (i.e., of the molecule, not the product) and synthetic co-surfactants (b) combined; the modifier is believed needed to ensure proper surfactant liquid crystal size (e.g., if domain size is too large, stability may be compromised).

wherein said liquid cleansing composition includes some portion in a surfactant liquid crystalline phase, as recognized by characteristic patterns observed via optical microscopy, or other established physical tests (e.g., x-ray diffraction);

wherein the shape of the thermal trace in a differential scanning colorimetry (DSC) experiment, by the method described below, is such that more than 50% of the transition enthalpy between 5° and 60° C. occurs in the window between 5° to 35° C., preferably between 5° to 30° C. (a reflection of the fact that sufficient surfactant is in liquid crystalline phase);

wherein said composition is stable (i.e., is physically stable and will not partition as can be visually observed) at 40° C. for at least 2 weeks.

It should be noted that the acyl isethionate surfactant of (a) and possibly (although not necessarily) some amount of fatty acid are brought into the final composition depending on what is the starting acyl isethionates "product". Thus, the starting "product" may be pure surfactant and contain no fatty acid, or it may comprise a mixture of acyl isethionates surfactant and fatty acids. In a co-pending application, applicants claim compositions in which the product (comprising at least 10% free fatty acid and/or fatty acid salt) is claimed.

It should be further noted that if a product comprising surfactant and fatty acids is used, the amount of surfactant or fatty acids in the final composition is less than the amount of these ingredients in the starting product. For example, without intending to limit the invention, if 10% surfactant in the final composition is desired, this might come from a starting product which is Dove® cleansing bar noodles, a mixture of DEFI flakes, fatty acids and fatty soaps as described in more detail below. Typically, such noodles comprise about 50% acyl isethionates surfactant along with fatty acid soap. Thus, to obtain 10% surfactant, about 20% noodles would be used. Therefore, if the surfactant has 35% fatty acid content, this results in about 7% (20% of 35%) fatty acid in final composition (counted as part of item (d)). As noted, at 50% surfactant content, this results in about 10% (20% of 50%) fatty acyl isethionates (counted as part of item (a)). As indicated, these examples are merely illustrative.

In a second embodiment, the invention relates to a process for making such compositions using acyl isethionate, co-surfactant, liquid crystal inducer and liquid crystal modifier as noted above.

The invention further relates to a method of ensuring liquid compositions comprising 1% to 30% fatty acyl isethionate surfactant can be formed regardless of the source of the fatty isethionates, that is to say, regardless of the fatty acid content of the fatty acid isethionates surfactant starting product and/or of the chain length of the fatty acyl group.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
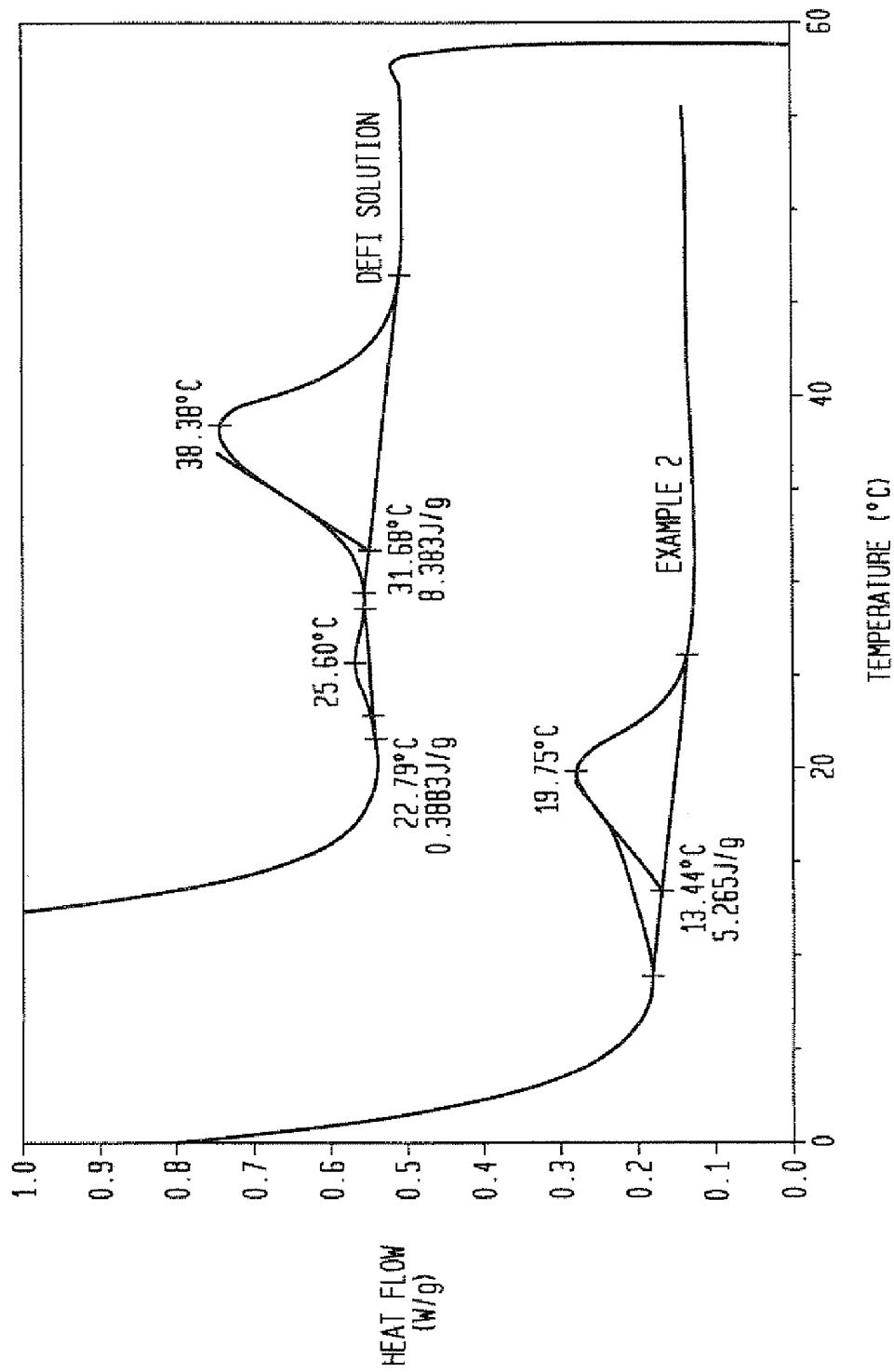
FIG. 1 is a differential scanning calorimetry (DSC) curve of a fatty acid isethionate solution typically used in preparing liquid DEFI compositions compared to Example 2 of the invention. The figure shows DEFI solution has a crystal transition peak around 38° C. compared to lower crystal transition peak of inventive example.

The present invention relates to novel liquid cleansing compositions comprising fatty acyl isethionate surfactant which compositions are viscous and very stable regardless of the level of free fatty acid or the chain lengths of the fatty acyl isethionate surfactant product (factors which typically affect stability and viscosity of compositions comprising acyl isethionates, especially at low and elevated temperature).

More specifically, the invention comprises liquid cleansing compositions comprising:

(a) 1 to 30% by wt. fatty acyl isethionate (which comes from the surfactant product; as indicated above, the amount of product needed to produce desired amount of fatty acyl isethionates depends on wt. % of fatty acyl isethionates in the starting product);

(b) 1 to 30% by wt. co-surfactant;

(c) 0.5 to 10% by wt. surfactant liquid crystal inducer selected from the group consisting of alkanolamide, alkylamineoxide and mixture of above and used to ensure that the liquid cleanser composition comprising (a) and (b) forms a liquid crystal phase at typical storage conditions; wherein said inducer is used in an amount of at least a certain percent (e.g., at least 10%) of fatty acyl isethionate and co-surfactant combined;

(d) 0.5 to 14% by wt. liquid crystal modifier which is straight chain fatty acids alone or is straight chain fatty acid in combination with straight chain alcohol and/or aliphatic hydrocarbon oil, wherein modifier is at least 10% of combined total of isethionates (a) (the molecule, not the surfactant product) and synthetic (b) combined;

wherein said liquid cleansing composition includes some portion in a surfactant liquid crystalline phase, as recognized by characteristic patterns observed via optical microscopy, or other established tests such as x-ray diffraction;

wherein the shape of the thermal trace in a differential scanning calorimetry (DSC) experiment conducted in accordance with the method described below, is such that more than 50% of the transition enthalpy between 5 to 60° C. occurs in the window between 5° to 35° C., preferably between 5 to 30° C.;

wherein said composition is stable (i.e., is physically stable and will not partition as can be observed visually) at >40° C. for at least 2 weeks.

The invention is defined in greater detail below.

DEFINITIONS

For purposes of this invention, a fatty acyl isethionate "product" comprises (in addition to other components) both pure acyl isethionates surfactant as well as free fatty acid and/or fatty acid salt.

Fatty Acyl Isethionate Surfactant

Compositions of the invention comprise 1 to 30% by wt., preferably 3 to 25% by wt. fatty acyl isethionate.

Fatty acyl isethionates surfactant are typically prepared by the reaction of an isethionates salt such as alkali metal isethionates and an aliphatic fatty acid having 8 to 20 carbon atoms and Iodine Value (measuring degree of unsaturation) of less than 20 g, for example:

where $R^1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Depending on the processing conditions used, the resulting fatty acyl isethionate product can be a mixture of 45 to 95% by weight of fatty acyl isethionates (as noted above, this is what provides the 1-30% recited as component (a)) and 40 to about 0 wt % of free fatty acids, in addition to isethionates salts, typically less than 5 wt. %, and trace (less than 2 wt. %) of other impurities. Generally a mixture of aliphatic fatty acids is used for the preparation of commercial fatty acyl isethionates surfactants. In the subject invention, it is preferred that the resulting fatty acyl isethionate surfactants (e.g., resulting from reaction of alkali metal isethionate and aliphatic fatty acid) have at least 20 wt % (on basis of fatty acyl isethionates reaction product) of fatty acyl group with 14 or more carbon atoms so that they form insoluble surfactant crystals in water at ambient temperature, and at least 16 wt. % of fatty acids with 14 or greater carbon atoms so that they also form insoluble surfactant crystals in water at ambient temperature. Formation of insoluble surfactant crystals can be determined using an optical microscope, or by measuring the crystal transition temperature of a 15 wt % fatty acyl isethionate aqueous solution with a pH in the range of 6.5 to 7.5 using differential scanning calorimetry (DSC) method described below. A fatty acyl isethionate surfactant solution formed by the above reaction typically has a thermal transition above 30° C. and below 60° C. A typical DSC thermal trace of fatty acyl isethionate solution is shown in FIG. 1. (top graph designated "DEFI Solution"). A key aspect of the present invention is that specific liquid inducers can shift the position of the thermal transition in the thermal trace to below 35° C., preferably below 30° C. where a surfactant liquid crystal phase can be formed, as shown in FIG. 1 for Example 2 of this invention (Composition of Example 2 is given in Table 1).

More specifically, the shape of the thermal trace by the DSC experiment is such that 50% of the transition enthalpy between 5 and 60° C. occurs in the window between 5 and 35° C., preferably between 5° and 30° C. We refer to this requirement of the transition enthalpy curve or trace in the DSC experiment as criteria for thermally trace. The resulting fatty acyl isethionate containing liquid cleansing composition is far more stable. In other words, without wishing to be bound by theory, by shifting the thermal transition of the acyl isethionate surfactant (actually of acyl isethionate and co-surfactant as described below), liquid crystals are far more readily formed and this enables the consistent use of material in a liquid composition which previously could not be readily used.

Particularly preferred fatty acyl isethionate products which may be consistently used include DEFI (Direct Esterification of Fatty Isethionate) flakes and synthetic detergent noodles produced from DEFI for personal cleanser application. DEFI flakes typically contain about 65 to 80 wt % of sodium fatty acyl isethionate and 15 to 30 wt % free fatty acids. More than 65 wt % of fatty acyl group of the resulting fatty acyl isethionates have 12 to 18 carbon atoms. Dove® cleansing bar noodles are mixtures of DEFI flakes described above and long chain (mainly C16 and C18) fatty acids and fatty soaps which contain about 40 to 60 wt % of fatty acyl isethionates and 25 to 40 wt % of fatty acids and fatty soaps. Examples of other commercial fatty acyl isethionates that may be used in this invention are Hostapon® surfactants from Clariant such as Hostapon® SCI185, Hostapon® SCI-78C, or Hostapon® SCI65C; Jordapon® surfactants from BASF such as Jordapon® CI prill or Jordapon® CI65; and sodium cocoyl isethionate from Yongan Daily Chemical Co. such as YA-SCI-85® or YA-SCI-65®.

As indicated, these fatty acyl isethionate products have not typically been used in preparation of personal liquid compositions because they readily form solid crystals TO (when used alone and/or with co-surfactant) and consequently make it very difficult to form stable liquids.

The amount of fatty acyl isethionates surfactants used in the liquid cleanser compositions of the present invention can be in the range of 1 up to 30 wt %, preferably 3 to 25 wt % of the liquid composition. The preferred level depends on the total amount of fatty acyl isethionates surfactants and other synthetic co-surfactants in the liquid cleanser of the present invention. The amount used should comprise of 20 to 90 wt %, preferably 40 to 80 wt % of this total amount of combined fatty acyl isethionates surfactant, and the synthetic co-surfactants described below.

Synthetic Co-Surfactants

A second component of the subject invention are surfactants selected from the groups consisting of anionic surfactants, nonionic surfactants, zwitterionic surfactants, amphoteric surfactants as described below. Such synthetic co-surfactants are believed to solubilize or partially solubilize fatty acyl isethionate surfactant described above. The amount of synthetic co-surfactant used in the present invention can be in the range of 1 to 30, preferably 3 to 25 wt % depending on the level of fatty acyl isethionate surfactant in the liquid composition. The amount of co-surfactant in the liquid composition should also be 10 to 80 wt % preferably 20 to 60 wt % of total weight of fatty acyl isethionates and synthetic co-surfactants of the liquid cleanser composition combined.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than at least 0.5, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, alkyl and acyl glycinates, alkyl suloacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and branched acyl isethionates.

Another class of anionics are carboxylates such as follows:

$$R-(CH_2CH_2O)_nCO_2M$$

wherein R is $C_8$ to $C_{20}$ alkyl; n is 1 to 20; and M is as defined above.

Another carboxylate which can be used is amido alkyl polypeptide carboxylates such as, for example, Monteine LCQ® by Seppic.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

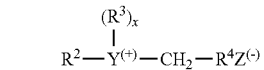

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

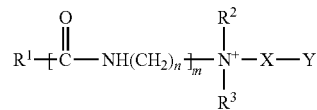

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Amphoacetates and diamphoacetates are also intended to be covered in possible zwitterionic and/or amphoteric compounds which may be used.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Other surfactants which may be used are described in U.S. Pat. No. 3,723,325 to Parran Jr. and "Surface Active Agents and Detergents" (Vol. I & II) by Schwartz, Perry & Berch, both of which are also incorporated into the subject application by reference.

Surfactant Liquid Crystal Inducers

Another essential ingredient of the present invention are the alkanoamides, alkylamineoxides or mixture of the above which function as surfactant liquid crystal inducer. The surfactant liquid crystal inducer is believed to be solubilized in the mixture of fatty acyl isethionates and synthetic cosurfactants as described above and to change the packing of surfactant micelles. Specifically, the inducer is believed to convert all or part of the fatty acyl isethionates and synthetic co-surfactants mixture to lamellar liquid crystals in the liquid cleanser composition of the invention. The fact that surfactant liquid crystals are induced in the cleanser composition of this invention can be confirmed by formation of thermal transition peak at a temperature between 5° to 35° C., preferably between 5° to 30° C., measured using the DSC method described below (compared to peaks typically formed at higher temperatures when inducer is not used, as seen in FIG. 1). A peak in the thermal trace at the relatively lower temperature is believed due to the formation of a surfactant liquid crystal phase when sufficient amount of surfactant liquid crystal inducer is added. The amount of liquid crystal inducer in the present invention can be 0.5 to 10 wt % of the liquid composition depending on total amount of fatty acyl isethionates and synthetic co-surfactants in the liquid composition. Specifically it should be at least 10 wt %, preferably 15 wt %, most preferably 20 wt % of the total fatty acyl isethionates and synthetic co-surfactants.

Both the level and the composition of the liquid crystal inducers required in the liquid composition of this invention can be determined by measuring the said cleanser composition of this invention containing various amount of liquid crystal inducer using the DSC method described below. It should be noted that a composition may have transition enthalpy peaks at temperatures both below and above 35° C. As noted, the cleanser composition of this invention (aqueous solution (e.g., isethionate plus co-surfactant plus inducer)) should meet the criteria for the thermal trace, i.e., have a thermal trace in the DSC experiment such that more than 50% of the transition enthalpy between 5° and 60° C. occurs in the window between 5° and 35° C., preferably between 5° and 30° C. More preferably, more than 60% of the transition enthalpy between 5° and 60° C. should occur in the window between 5° and 35° C. Even more preferably, more than 60% (theoretically, there is no upper limit) of the transition enthalpy between 5° and 60° C. occurs in the window between 5° and 30° C.

When such conditions are met, this indicates that the type and amount of inducer and amount of modifier, as discussed below, have been correctly selected and the cleansing composition will be stable, i.e., not show visible signs of physical separation for at least two weeks, preferably at least 4 weeks when stored at 40° C. The DSC curves of a cleanser composition without inducer compared to a composition of the invention with inducer (Example 2) are both shown in FIG. 1.

Examples of liquid crystal inducing compounds which may be used include but are not limited to alkanolamides such as mono- and di-ethanolamides, N-methyl-monoethanolamide, isopropanolamides of fatty acids having about 10 to 20 carbon atoms, and PPG-hydroxyethyl cocamides and alkylamineoxide with carbon chain length in the range of 10 to 20. Specific examples of suitable compounds include cocomonoethanolamide, cocodiethanolamide, lauryl mono/or di ethanol amide, coco mono/or di isopropanolamide, lauryl mono/or di ethanolamide, myristyl mono/or di ethanolamide, cocoyl N-methyl-monoethanolamide, cocoylamineoxide, laurylamineoxide, myristylamineoxide, and polypropylene glycol-2-hydroxyethyl cocoamide. Particularly useful ingredients for this invention are cocomono or diethanol amide, lauryl mono/or di ethanol amide, lauryl amine oxide and coco amine oxide.

Liquid Crystal Modifier

A fourth critical ingredient of the liquid cleanser composition of this invention is surfactant liquid crystal modifier These modifiers include straight chain fatty acids alone; or mixture of straight chain fatty acids, with either straight chain fatty alcohols and/or aliphatic hydrocarbons. These ingredients are believed critical to increase the liquid viscosity and to achieve its storage stability at both ambient and elevated temperatures due to the formation of more surfactant liquid crystal phase than if these modifiers were not present.

While not wishing to be bound by theory, it is believed that the liquid crystal phase present is lamellar phase and the lamellar phase is present at least in part in the form of vesicles, wherein the liquid crystal modifier is believed to alter the size of the vesicles such that at least some portion of the vesicles are smaller than 5 microns. It is believed that vesicles smaller than 5 microns, preferably smaller than 2 microns impart greater physical stability to the cleansing composition.

It is known that surfactant liquid crystals generally (such as the ones induced by mixture of fatty acyl isethionate, synthetic co-surfactant and alkanolamide/or alkylamineoxide according to the subject invention) can have various size and shapes. However, to achieve combination of high viscosity and simultaneously good product stability at various storage conditions, an adequate phase volume of surfactant liquid crystal lamellar vesicles are believed to be needed. Optical microscopy cannot determine the phase volume of the surfactant liquid crystal phase; however, this technique can be used to determine whether lamellar liquid crystals have been formed by observation using a high magnification optical microscope with cross-polarized light setting.

Figure 4:
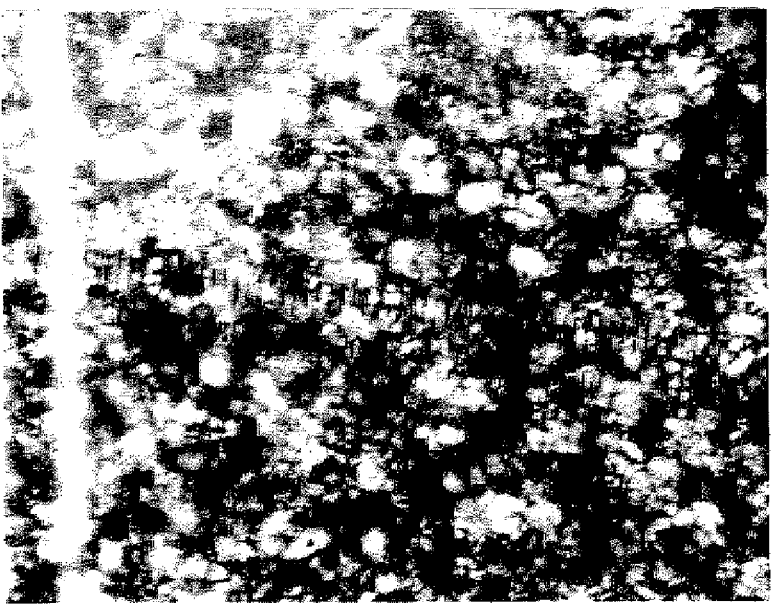
FIG. 4b (Figure at bottom of FIG. 4) is an optical micrograph of surfactant liquid crystal composition where sufficient liquid crystal modifier has been added to have a sufficiently large phase volume of liquid crystal phase to provide good phase stability.
FIG. 4a (Figure at top of FIG. 4) shows the liquid crystal domain without sufficient surfactant liquid crystal modifier and which is therefore subject to visible phase separation.
Figure 4:
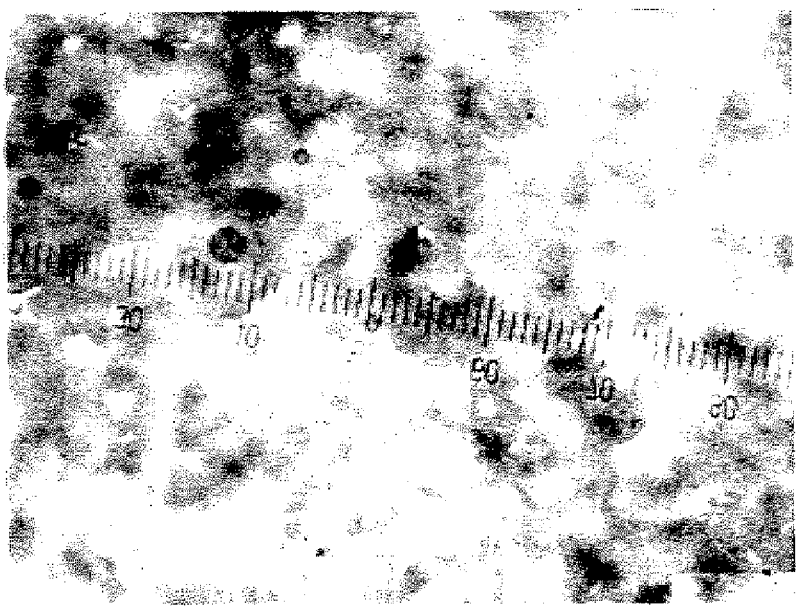

Under the cross polarized light optical microscope, these liquid crystals appear as shiny domains. There are regular patterns that define lamellar liquid crystal phase, as noted in the literature by Rosevear, Journal of the Oil Chemists' Society (1954), Vol. 31, page 628 (which reference is hereby incorporated by reference into the subject application). Examples of a typical surfactant liquid crystal optical micrograph are shown in FIGS. 4a and 4b without or with sufficient amount of liquid crystal modifier respectively. FIG. 4a, without the liquid crystal modifier, represents comparative example D of Table 2 and shows large irregular liquid crystal domains. The composition is not stable at ambient temperature, since it is believed that stability requires the presence of some portion of the liquid crystals to be vesicles 5 microns or less, preferably 2 microns or less in diameter. It is not possible to define exactly how large the portion is but, if a sufficiently large portion is obtained, this is confirmed by DSC test of the invention.

Thus, the composition which does have a sufficient amount of liquid crystal modifier (Example 2 of Table 1) displays a considerable amount of lamellar liquid crystal phase with size less than 2 micron in diameter when observed via optical microscopy. As indicated, the fact that it has "sufficient" modifier is confirmed because the composition, meets the criteria for the DSC thermal trace, and is stable at ambient and at 40° C. for over one month.

Liquid cleanser compositions which do not contain sufficient amount of liquid crystal modifier show phase separation and contain lamellar liquid crystal with size of 10 microns or larger in diameter. Specifically, without sufficient modifier, the compositions separate after storage at ambient temperature in less than 2 weeks. As noted, it was found that this phase separation problem can be overcome in the subject invention by adding sufficient level of the liquid crystal modifiers to reduce the size of the lamellar liquid crystal and also possibly to increase the phase volume of the liquid crystal phase (which in turn is reflected by observation using the optical microscope or by the defined DSC enthalpy characterization).

It should be noted that) other than the desired surfactant liquid crystal phase described above, the liquid compositions of the subject invention might also contain other surfactant phases such as surfactant micelles and insoluble surfactant crystals.

If the fraction of surfactant liquid crystal phase in the resulting liquid composition of the invention is not visible using optical microscopy, the presence in the liquid composition of this invention can also be confirmed by an alternate method like small-angle X ray scattering. In an x-ray scattering experiment, the presence of lamellar phase is indicated by diffraction lines at positions d, d/2, d/3, wherein d is the Bragg spacing. P. Linder, T. Zemb, "Neutrons, X-rays and Light: Scattering Methods Applied to Condensed Matter", Eisevier (Boston, 2004).

Thus, as seen, for the invention it is critical that two things occur simultaneously: (1) the liquid crystal inducer is required to ensure at least some portion surfactant phase is in lamellar liquid crystal phase; and (2) the modifier is required to ensure the composition is physically stable. It is believed that physical stability occurs because a portion of the lamellar phase is in the form of small vesicles of 5 microns or less, preferably 2 microns or less in diameter. However, whatever the reason, when the composition of the invention is prepared as noted (proper selection of ingredients), this is reflected in the DSC trace and stability as defined.

The liquid crystal modifiers suitable for the present invention are straight chain fatty acids, straight chain fatty alcohols and hydrocarbon oils with molecular weight less than 600, preferably less than 400 g per mole, and the total level can be in the range of 0.5 to 14 wt % of the liquid cleanser composition depending on total amount of fatty acyl isethionates and synthetic cosurfactants described above. It should be noted that fatty acids and fatty soaps contained in the fatty acyl isethionate surfactant composition are considered to be part of the liquid crystal modifier. The total level of liquid crystal modifier should be at least 15 wt %, preferably 20 wt % of total amount of fatty acyl isethionate surfactant (not the product) and synthetic co-surfactants in the liquid cleanser composition of this invention. Examples of useful ingredients which form small surfactant liquid crystals from the mixture of fatty acyl isethionate, synthetic co-surfactants and crystal inducer (alkanolamide/or alkylamine oxide) include straight chain fatty acids of $C_8$ to $C_{20}$ hydrocarbons such as capric acid, lauric acid, palmitic acid, and stearic acid; fatty alcohols of $C_8$ to $C_{20}$ straight chain; and hydrocarbon oils of 9 to 40 hydrocarbons, preferably 9 to 30 linear hydrocarbon oil, even more preferably 10-24 linear hydrocarbon oil. Branched fatty acids or branched fatty alcohols such as isostearic acid and isostearic alcohol are optional ingredients. If used, these are preferably limited to no more than 30 wt %, most preferably no more than 20 wt % of total liquid crystal modifiers (i.e. fatty acids, fatty alcohols and hydrocarbon oils). If mixture of fatty acids and fatty alcohols are used as the liquid crystal modifier, the percentage of fatty acids is preferably more than 50 wt %, most preferably more than 60 wt % of total amount of fatty acids and fatty alcohols in the liquid composition of this invention. To provide good lather, long chain fatty acids and fatty alcohols with carbon chain length 16 or higher are preferably no more than 6 wt % in the liquid composition of this invention and no more than 50 wt % of total amount of fatty acyl isethionate and synthetic cosurfactant described above.

Water Soluble/Dispersible Polymers

Water soluble/dispersible polymers are an optional ingredient that is highly preferred to be included in the liquid composition of the invention. The water soluble/or dispersible polymer can be cationic, anionic, amphoteric or nonionic polymer with molecular weight higher than 100,000 Dalton. These polymers are known to enhance in-use and after-use skin sensory feels, to enhance lather creaminess and lather stability, and to increase the viscosity of liquid cleanser compositions. In this invention, these polymers, particularly gel forming polymers such as starch granule, xanthan gum, Carbopol®, cross-linked alkaline soluble emulsion polymers and cationic guar gums such as Jaguar® C13S, are found to be useful for some fatty acyl isethionate and co surfactant composition (e.g., compositions having combination of fatty acyl isethionate and cocoamidopropyl betaine) to form the desired surfactant liquid crystals in the liquid composition of this invention. This is believed due to the increase of effective surfactant concentration in the aqueous phase of the liquid cleansing composition in the presence of these gel forming polymers.

Examples of water soluble/or dispersable polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum arabic, gum acacia, gum agar, xanthan gum and mixtures thereof; modified and nonmodified starch granules with gelatinization temperature between 30 to 85° C. and pregelatinized cold water soluble starch; polyacrylate; Carbopols; alkaline soluble emulsion polymer such as Aculyn 28, Aculyn 22 or Carbopol Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrosoft Um-200; and Polyquaternium-24.

Gel forming polymers such as modified or nonmodifed starch granules, xanthan gum, Carbopol, alkaline-soluble emulsion polymers and cationic guar gum such as Jaguar C13S, and cationic modified cellulose such as UCARE Polymer JR 30 or JR 40 are particularly preferred for this invention.

Water Soluble Skin Benefit Agents

Water-soluble skin benefit agents another optional ingredient that is preferred to be included in the liquid compositions of the invention. A variety of water-soluble skin benefit agents can be used and the level can be from 0 to 50 weight %, preferably 1 to 30%. The materials include, but are not limited to, polyhydroxy alcohols such as glycerol, propylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerol, sorbitol and propylene glycol.

The liquid cleansing composition of the invention also may comprise 0 to 50% by wt., preferably 1 to 30 by wt., more preferably 2 to 20% benefit agent.

One class of ingredients are nutrients used to moisturize and strengthen, for example, the skin. These include:
a) vitamins such as vitamin A and E, and vitamin alkyl esters such as vitamin C alkyl esters;
b) lipids such as cholesterol, cholesterol esters, lanolin, creaminess, sucrose esters, and pseudo-ceramides;
c) liposome forming materials such as phospholipids, and suitable amphophilic molecules having two long hydrocarbon chains;
d) essential fatty acids, poly unsaturated fatty acids, and sources of these materials;
e) triglycerides of unsaturated fatty acids such as sunflower oil, primrose oil avocado oil, almond oil;
f) vegetable butters formed from mixtures of saturated and unsaturated fatty acids such as Shea butter;
g) minerals such as sources of zinc, magnesium, and iron;

A second type of skin benefit agent is a skin conditioner used to provide a moisturized feel to the skin. Suitable skin conditioners include:
a) silicone oils, gums and modifications thereof such as linear and cyclic polydimethylsiloxanes, amino, alkyl, and alkyl aryl silicone oils;
b) hydrocarbons such as liquid paraffins, petrolatum, Vaseline, microcrystalline wax, ceresin, squalene, pristan, paraffin wax and mineral oil;
c) conditioning proteins such as milk proteins, silk proteins and glutens;
d) cationic polymers as conditioners which may be used include Quatrisoft LM-200 Polyquaternium-24, Merquat Plus 3330—Polyquaternium 30; and Jaguar® type conditioners;
e) humectants such as glycerol, sorbitol, and urea;
f) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:
a) antimicrobials such as 2-hydroxy-4,2',4'-trichlorodiphenylether (DP300) 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc salts, tea tree oil,
b) anti-acne agents such as salicylic acid, lactic acid, glycolic acid, and citric acid, and benzoyl peroxide (also an antimicrobial agent),
c) oil control agents including sebum suppressants, modifiers such as silica, titanium dioxide, oil absorbers, such as micro sponges,
d) astringents including tannins, zinc and aluminum salts, plant extracts such as from green tea and Witch-hazel (Hammailes),
e) scrub and exfoliating particles, such as polyethylene spheres, agglomerated silica, sugar, ground pits, seeds, and husks such as from walnuts, peach, avocado, and oats, salts,
f) cooling agents such as methanol and its various derivatives and lower alcohols,
g) fruit and herbal extracts,
h) skin calming agents such as aloe vera,
i) essential oils such as mentah, jasmine, camphor, white cedar, bitter orange peel, rye, turpentine, cinnamon, bergamot, *citrus unshiu*, calamus, pine, lavender, bay, clove, hiba, eucalyptus, lemon, starflower, thyme, peppermint, rose, sage, menthol, cineole, sugenol, citral, citronelle, borneol, linalool, geraniol, evening primrose, camphor, tymol, spirantol, penene, limonene and terpenoid oils.

Other benefit agents that can be employed include antiaging compounds, sunscreens, and in lightening agents.

When the benefit agent is oil, especially low viscosity oil, it may be advantageous to pre-thicken it to enhance its delivery. In such cases, hydrophobic polymers of the type describe in U.S. Pat. No. 5,817,609 to He et al. may be employed, which is incorporated by reference into the subject application.

The final liquid cleanser composition of the present invention should have a viscosity more than 150, preferably greater than 250 Pas measured at 0.01 rps determined by a Rheometric Scientific SR5 Rheolmeter at 25° C., preferably at 10° C., 25° C. and 40° C.; and pH between 5.5 to 8.0, preferably 6.0 to 7.5, following the methodology for viscosity determination described below. It should have a thermal trace in a DSC experiment such that more than 50% of the transition enthalpy in transition enthalpy area between 5° and 60° C. occurs in the window between 5° and 35° C., preferably between 5° and 30° C.

The compositions should also be physically phase stable at room temperature and 40° C. for at least two weeks.

Other Optional Components

In addition, the compositions of the invention may include 0 to 15% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenyl ether (DP300); preservatives such as dimethyloldimethylhydantoin (Glydant XL 1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330—Polyquaternium 30; and Jaguar® type conditioner.

Polyethylene glycols as conditioners which may be used include:

| Polyox | WSR-25 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

EXAMPLES & PROTOCOL

Methodology of Differential Scanning Calorimetry (DSC)

Figure 2:
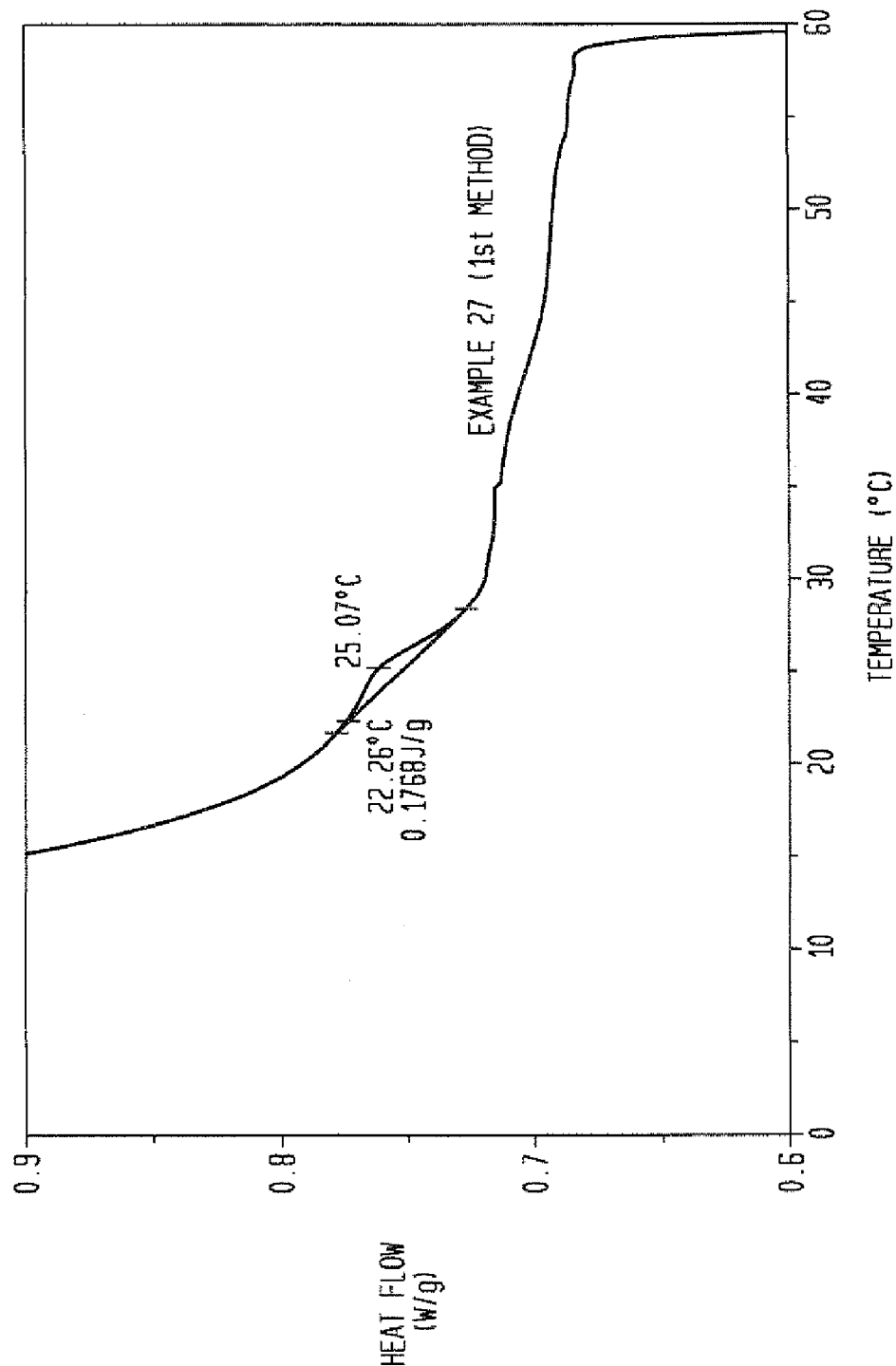
FIG. 2 is DSC method measured using the first defined protocol and showing how the peak may be masked by the water melting (e.g., for example 27). In such case, a second protocol must be used.
Figure 3:
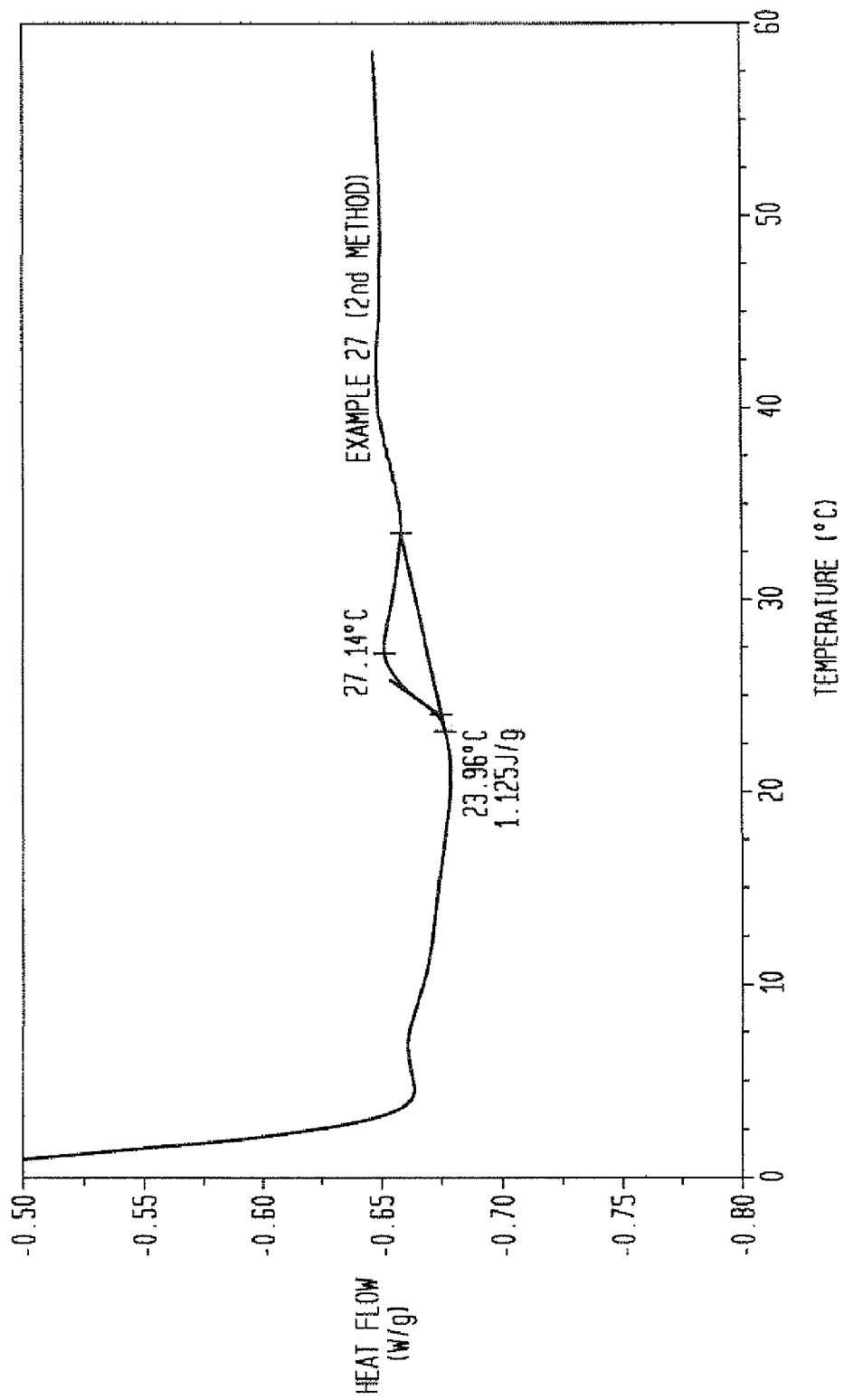
FIG. 3 is a second DSC protocol used so that the peak can be seen (e.g., again for example 27).

Samples were weighed into an aluminum pan, hermetically sealed, and loaded into a 2920 MDSC machine from TA Instruments at 25° C. Depending on the interference of water melting peak (normally this peak varies from −10 to 25 C) with the surfactant liquid crystal transition temperature, two protocols were used for the DSC measurement. All the liquid compositions were first measured using the first protocol described as following. The sample was equilibrated to a temperature of −35° C., Iso-Track for 2 minutes followed by heating at 10° C./min to 60° C. Transition enthalpies were evaluated using the standard software from TA Instruments. A typical resulting DSC curve measured using Example 2 of this invention in Table 1 is shown in FIG. 1. If the water melting peak interfered with the transition temperature of liquid composition between 5 to 35 C as shown in FIG. 2 for Example 27 of Table 3, then the second DSC method should be used for the measurement. In the second DSC protocol, liquid composition was equilibrated to a temperature of 1.5° C., Iso-Track for 2 minutes followed by heating at 5° C./minute to 60° C. DSC curve of Example 27 measured using the second DSC protocol was shown in FIG. 3.

Methodology for Viscosity Measurement

Viscosity was measured using either SR-5 Rheometer from Rheometric Scientific or AR-G2 Rheolometer from TA Instruments. Procedures and set up for each rheometer to measure the cleanser's viscosity are described below:

Instrument: SR-5 from Rheometric Scientific
    Geometry: Cone and Plate
    Diameter: 25 mm
    Cone Angle: 5.69°
    GAP: 0.056 mm
    Experimental Conditions:
    Test type: Steady Rate Sweet
    Shear Rate Ramp: from 0.01 to 100 (log mode, 5 points per decade)
    Measurement Time: 20 seconds
    Temperature: Various (10° C./25° C./40° C.)

Procedure:

About 0.5 g of sample was poured on to the plate. Cone was lowered to the gap of 0.1 mm and excess of sample was removed using plastic spatula. Gap was reduced to 0.056 mm and test was started. Shear rate vs. viscosity were plotted.

Alternative Instrument: AR-G2 from TA Instruments
    Geometry: Cone and Plate
    Diameter: 40 mm
    Cone Angle: 2°
    GAP: 0.061 mm
    Experimental Conditions;
    Test Type: Steady Rate Sweep
    Shear Rate Ramp: from 0.01 to 100 (log mode, 5 points per decade)
    Measurement Time: 40 seconds
    Temperature: Various (10° C./25° C./40° C.)

Procedure:

About 0.5 g of sample was poured on to the plate. Cone was lowered to the gap of 0.1 mm and excess of sample was removed using plastic spatula. Gap was reduced to 0.061 mm and test was started. Shear rate vs. viscosity were plotted.

Examples of compositions of the invention are set forth below:

Examples: 1 to 12

TABLE 1

| | Example number | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| DEFI (Directly esterified fatty acid isethionate) | 12 | 12 | 12 | 12 | 12 | 12 | — | — | — | 12 | 12 | 12 |
| CoCo Ise 75% | — | — | — | — | — | — | 12 | — | — | — | — | — |
| Jodapan Cl | — | — | — | — | — | — | — | 12 | — | — | — | — |
| Dove ®# | — | — | — | — | — | — | — | — | 12 | — | — | — |
| Cocoamidopropyl Betaine | 8 | 8 | 8 | 3 | 8 | 8 | 8 | 8 | 8 | — | 2 | — |
| Na lauryl amphoacetate | — | — | — | — | — | — | — | — | — | 8 | — | — |
| Na lauryl 2EO sulfate | — | — | — | — | — | — | — | — | — | — | 6 | — |
| Na lauryl sulfosuccinate | — | — | — | — | — | — | — | — | — | — | — | 8 |
| Lauric acid (Modifier) | 2 | 2 | 1 | 2 | — | 2 | 2 | 3 | 2 | 2 | 2 | 2 |
| ASAD* (Modifier) | — | — | — | 3 | — | — | — | — | — | — | — | — |

TABLE 1-continued

| | Example number | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Cocomonoethanol amide (Inducer) | 4 | 6 | 6 | 6 | 6 | — | 4 | 6 | 5 | 5 | 5 | 5 |
| Laurylamine oxide (Inducer) | — | — | — | — | — | 4 | — | — | — | — | — | — |
| Glycerin | 5.0 | 5.0 | 5.0 | 5.0 | 5.0 | 5.0 | 5.0 | 5.0 | 5 | 5 | 5 | 5 |
| Cationic Polymer | 0.2 | 0.2 | 0.2 | 0.2 | 0.2 | 0.2 | 0.2 | 0.2 | 0.2 | 0.2 | 0.2 | 0.2 |
| Pure Gel B990 (starch ex. Grain Processing) | 6 | 6 | 6 | 6 | 6 | 6 | 6 | 6 | 2 | 2 | 6 | 6 |
| Petrolatum (Penreco Snow white) | 6 | 6 | 6 | 6 | 6 | 6 | 6 | 6 | 6 | 6 | 6 | 6 |
| Hydantoin Preservative | 0.1 | 0.1 | 0.1 | 0.1 | 0.1 | 0.1 | 0.1 | 0.1 | 0.1 | 0.1 | 0.1 | 0.1 |
| Perfume | 1.0 | 1.0 | 1.0 | 1.0 | 1.0 | 1.0 | 1.0 | 1.0 | 1.0 | 1.0 | 1.0 | 1.0 |

*ASAD: mixture of 45% stearic and 55% palmitic acid.
Dove ® bar, as unfragranced noodles.

Examples 1 to 12 were prepared by mixing all the ingredients except perfume and glydant plus at 70 to 75° C. for 15 to 30 minutes until all the solid ingredients such as DEFI, lauric acid, ASAD (mixture of fatty acids) and cocomonoethanolamide, CMEA (liquid crystal inducer) dissolved to form an uniform mixture. 0.2 to 0.4 wt % of NaOH was added to the liquid during the heating of the liquid to neutralize some of the fatty acid in the liquid composition. Perfume and glydant plus (a hydantoin preservative) were added after the liquid was cooled below 40° C. The pH of these liquids was adjusted to 6.7 to 7.1 using either 30% citric acid or 25% NaOH solution. Samples were stored at room temperature and 40° C. for over 4 weeks. All the samples were stable after storage for over 4 weeks, without visible physical separation.

Both DEFI and Dove® are fatty acyl isethionate products manufactured by Unilever. DEFI has 65-80 wt % of C8 to C18 fatty acyl isethionates and 15-30 wt % free fatty acids of 8 to 18 carbons. Dove® is prepared by mixing 65-75 wt % of DEFI with 15-25 wt % of long chain (C16 to C18) fatty acid and fatty soap. Cocolse 75% (ex. Huanggang Yongan Daily Chemical Co.) is mixture of 70 to 76 wt % of sodium cocoyl isethionate and 13 to 20 wt % of free cocoyl fatty acid. Jordapon® CI from BASF contains more than 84 wt % of sodium cocoyl isethionate and less than 8 wt % of free cocoyl fatty acid. These examples indicate that this invention are robust to stabilize fatty acyl isethionates of different compositions (i.e., when used with liquid crystal inducer and liquid crystal modifier, compositions are consistently stable at both high and low temperature for at least 4 weeks regardless of fatty acid content and/or chain length of fatty acyl group) and are useful for a variety of co-surfactants (e.g., amphoacetate, sulfosuccinates).

Eight comparative examples using cocoamidopropyl betaine as the cosurfactant with composition shown in Table 2 were prepared for comparison. All the comparative examples were prepared the same way as Examples 1 to 12. None of these samples were stable at both 40° C. and at room temperature storage condition due to the lack of one of the required ingredients needed to stabilize the liquid composition. Specifically, Comparative Examples A, B and C had no CMEA (liquid crystal inducers; these are believed needed since the modifier works only when surfactant phase of composition is in sufficiently liquid crystal form), for example. Comparative example D did not have sufficient free fatty acid or other modifier required to form a stable, surfactant liquid phase, perhaps because the liquid crystals have unstably large domain size. Comparative example E had no co-surfactant (believed necessary to help form liquid crystals). Comparative F had no hydrocarbon oil, e.g., petrolatum. Again, without wishing to be bound by theory, this may have hindered formation of small particle domains and affected stability. Comparative examples G and H contain all the required ingredients in the composition. However, the amount of CMEA or lauric acid used in the liquid is not sufficient to maintain its physical stability (once more, without wishing to be bound by theory, because not sufficient to induce liquid crystal phase and/or, if sufficient to induce liquid crystal phase, not sufficient to form proper domain size). The stability of Comparative examples G and H can be achieved by increasing the level of CMEA and/or lauric acid as shown in Example 1, 2 and 3 of Table 1.

It should be noted in general that the level of alkanoamide such as CMEA, or of hydrocarbon oils, to form the stable liquid composition of this invention also depends on the combination of fatty acyl isethionate and synthetic cosurfactant. This is exemplified in Examples 22 to 31 of Table 4.

TABLE 2

| | Comparative examples | | | | | | | |
|---|---|---|---|---|---|---|---|---|
| | Comparative Examples | | | | | | | |
| | A | B | C | D | E | F | G | H |
| DEFI | 12 | 12 | 12 | 12 | 18 | 12 | 12 | 12 |
| Cocoamidopropyl Betaine | 8 | 8 | 8 | 8 | 0 | 8 | 8 | 8 |
| Lauric acid | — | — | 2 | — | 1 | 2 | 1 | 1 |
| ASAD | — | 3 | — | — | — | — | — | — |

TABLE 2-continued

|  | Comparative examples |  |  |  |  |  |  |  |
|---|---|---|---|---|---|---|---|---|
|  | Comparative Examples |||||||| 
|  | A | B | C | D | E | F | G | H |
| Cocomonoethanolamide | — | — | — | 6 | 6 | 6 | 2 | 4 |
| Glycerin | 5.0 | 5.0 | 5.0 | 5.0 | 5.0 | 5 | 5.0 | 5.0 |
| Jaguar C13S | 0.2 | 0.2 | 0.2 | 0.2 | 0.2 | 0.2 | 0.2 | 0.2 |
| Pure Gel B990 (starch, Grain processing) | — | — | 6 | 6 | 6 | 6 | 6 | 6 |
| Petrolatum (Penreco snow white) | 6 | 6 | 6 | 6 | 6 | — | 6 | 6 |
| Glydant plus (Hydantoin) | 0.1 | 0.1 | 0.1 | 0.1 | 0.1 | 0.1 | 0.1 | 0.1 |
| Perfume | 1.0 | 1.0 | 1.0 | 1.0 | 1.0 | 1.0 | 1.0 | 1.0 |

Examples 13 to 21

Liquid Composition with Various Water Soluble Polymers and Skin Benefit Agents

TABLE 3

|  | Examples |||||||||  Comparative examples ||
|---|---|---|---|---|---|---|---|---|---|---|---|
|  | 13 | 14 | 15 | 16 | 17 | 18 | 19 | 20 | 21 | I | J |
| DEFI | 12 | 12 | 12 | 12 | 12 | 9.6 | 12 | 12 | 12 | 12 | 12 |
| Cocoamidopropyl betaine | 8 | 8 | 8 | 8 | 8 | 6.4 | 8 | 8 | 8 | 8 | 8 |
| Lauric acid | 3 | 3 | 3 | 3 | 3 | 1.6 | 0 | 2 | 2 | 2 | 2 |
| Lauryl alcohol | — | — | — | — | — | — | 2 | — | — | — | — |
| Cocomonoethanolamide | 6 | 5 | 5 | 5 | 5 | 3.8 | 4 | 4 | 4 | 4 | 4 |
| Glycerin | 5 | 5.0 | 5.0 | 5.0 | 30 | 4.8 | 5 | 5 | 5 | 5 | 5 |
| Jaguar C13S | 0.2 | — | — | — | 0.2 | 0.16 | 0.2 | 0.2 | 0.2 | 0.2 | 0.2 |
| Methocel 40–101 (ex. Dow Chemical) | — | 0.75 | — | — | — | — | — | — | — | — | — |
| Waterlock A18 (starch, Grain processing) | — | — | 1.0 | — | — | — | — | — | — | — | — |
| ETD2020 (Carbopol from Noveon) | — | — | — | 0.5 | — | — | — | — | — | — | — |
| Pure Gel B990 (starch, Grain processing) | — | — | — | — | 2 | 2.4 | 4 | 4 | 4 | 4 | 4 |
| Petrolatum (Penreco snow white) | 6 | 6 | 6 | 6 | 6 | 30 | — | — | 1 | — | — |
| Mineral oil (40 Oil ex Sonneborn) | — | — | — | — | — | — | 1 | 1 | — | — | — |
| Sunflower seed oil | — | — | — | — | — | — | — | 6 | — | 6 | — |
| Silicone oil 60,000 cps | — | — | — | — | — | — | — | — | 6 | — | 6 |
| Glydant | 0.2 | 0.2 | 0.2 | 0.2 | 0.2 | 0.2 | 0.2 | 0.2 | 0.2 | 0.2 | 0.2 |
| Perfume Dove ® | 1.0 | 1.0 | 1.0 | 1.0 | 1.0 | 0.8 | 1.0 | 1.0 | 1.0 | 1.0 | 1.0 |

Examples 13 to 21 of present invention except example 18 were prepared using the method same as the one described in example 1. Examples 18 was prepared by adding petrolatum to the liquid composition after the liquid was cooled below 30° C. and mixed at low speed to form large petrolatum droplet in the liquid (more than 500 μm). The sample was then passed through 60-mesh screen once to make petrolatum droplet with size in the range of 20 to 800 μm. All the samples are stable at both 40° C. and room temperature for over 4 weeks except comparative example I and J which did not contain hydrocarbon oils such as mineral oil or petrolatum. Stability of these 2 examples can be achieved by adding low level of hydrocarbon oil into the liquid composition as shown in Examples 20 and 21 (the sensitivity of stability can be noted by the fact that adding just 1% more liquid crystal modifier, which we believe affects domain size of liquid crystal phase, permits composition to go from instability to stability); or by increasing the amount of water soluble/dispersible polymer in the liquid composition.

Various type of water soluble or water swellable polymers were used to make Examples 13 to 16. Jaguar C13S is cationic cellulose ex. Rhodia, Methocel 40-101 is hydroxymethylcellulose from Dow, Water Lock A18 is modified starch super absorbent polymer available from Grain Processing, and ETD 2020 is cross linked polyacrylic acid from Noveon. All these water soluble/dispersible polymers are very compatible with the liquid compositions of this invention. Examples 17 and 18 show that the liquid composition of this invention can have high level of humectants such as 30% glycerin or high level of emollient oils such as petrolatum to deliver afterwash soft smooth moisturizing skin benefit.

Examples 22 to 31

|  | Examples | | | | | | | | | |
| --- | --- | --- | --- | --- | --- | --- | --- | --- | --- | --- |
|  | 22 | 23 | 24 | 25 | 26 | 27 | 28 | 29 | 30 | 31 |
| DEFI | 9.6 | 12 | — | — | — | — | — | — | — | — |
| Dove ®# | — | — | — | — | — | 12 | 17 | 8 | 16 | 30 |
| Jodapon Cl | — | — | 8.5 | 8.5 | 8.5 | — | — | 2 | 0 | 0 |
| Na lauryl amphoacetate | 2.4 | — | — | — | — | — | — | — | — | — |
| Cocoamidopropyl Betaine | — | 3 | 2 | 2 | 2 | 2 | 2 | 2 | 6 | 1 |
| Na lauryl 1EO sulfate | 4.0 | 2.5 | 5 | 5 | 5 | 5 | 5 | 5 | 4 | 2 |
| Na lauryl sarcosinate | — | 2.5 | — | — | — | — | — | — | — | — |
| ASAD* | — | — | 4.5 | 7.5 | — | — | — | — | — | — |
| Cocomonoethanol amide | 4 | 3 | 4 | 4 | 4 | 4 | 4 | 2 | 4 | 4 |
| Lauric acid | 2.0 | 1 | 3 | 0 | 7.5 | 2.0 | 2.0 | 2 | 1.0 | — |
| Lauryl alcohol | — | 0.5 | — | — | — | — | — | — | — | — |
| Glycerin | 5 | 5 | 5 | 5 | 5 | 5 | 5 | 5 | 5 | — |
| Jaguar C13S | 0.2 | — | 0.2 | 0.2 | 0.2 | 0.2 | 0.2 | 0.2 | — | — |
| Starch Pure Gel B990 | 1.5 | — | — | — | — | 3.0 | — | 1 | — | — |
| Mineral oil 40 | — | — | 1.0 | 1.0 | 1.0 | 1.0 | — | 1.0 | 1.0 | 2 |
| Petrolatum | — | 30 | — | — | — | — | — | — | — | — |
| Glydant plus | 0.2 | 0.2 | 0.2 | 0.2 | 0.2 | 0.2 | 0.2 | 0.2 | 0.2 | 0.2 |
| Perfume | 0.8 | 0.8 | 0.8 | 0.8 | 0.8 | 0.8 | 0.8 | 0.8 | 0.8 | 0.8 |

*ASAD: mixture of 45% stearic and 55% palmitic acid
Dove ® bar, as unfragranced noodles Examples 22 to 31 of the present invention were prepared using the method same as the one described in example 1 to show liquid cleanser composition of this invention can be prepared using various combination of synthetic surfactants (Example 22, 23), high level of straight chain fatty acids (51% of total fatty acyl isethionate and synthetic cosurfactants, Examples 24, 25 and 26), or mixture of fatty acyl isethionates (Example 29). Examples 22, 28 were prepared to show liquid cleanser composition of this invention can be stabilized by using fatty acids alone as the liquid crystal modifier. Liquid composition of this invention can also be prepared without using water soluble or dispersible polymer as shown in Examples 23, 30 and 31.

The invention claimed is:

1. A personal liquid cleanser composition comprising:
   (a) 1 to 30% by wt of fatty acyl isethionates;
   (b) 1 to 30% by wt. of a co-surfactant selected from the group consisting of anionic, nonionic, amphoteric, zwitterionic synthetic surfactants and mixture of above;
   (c) 0.5 to 10% by wt. of alkanolamide selected from the group consisting of mono- and di-ethanolamides, N-methyl-monoethanolamide, isopropanolamides of fatty acids having about 10 to 20 carbon atoms, and PPG-hydroxyethyl cocamides wherein the amount of said alkanolamide is ≧15 wt% of total amount of items a and b;
   (d) 0.5 to 14 wt% of straight chain fatty acids; or mixture of straight chain fatty acids with straight chain fatty alcohols and/or aliphatic hydrocarbon oils;
   wherein said straight chain fatty acid with a chain length of $C_{16}$ or higher comprises no more than 6 wt. % of the liquid cleaner and no more than 50 wt. % of total of (a) and (b);
   wherein total amount of straight chain fatty acids, straight chain fatty alcohols and aliphatic hydrocarbon oils is used at a level of at least 10% of fatty acyl isethionates (a) and synthetic cosurfactants (b) in combination
   wherein said liquid cleansing composition contains liquid crystalline-phase, as recognized by characteristic patterns observed via optical microscopy or x-ray diffraction;
   wherein the final composition has a thermal trace in a differential scanning colorimetry (DSC) experiment such that more than 50% of the transition enthalpy measured between 5 and 60° C. occurs in the window from 5 to 35° C.; and
   wherein the composition is stable at 40° C. for at least 2 weeks wherein said thermal trace and said stability confirm that sufficient components (c) and (d) have been added to induce formation of sufficient liquid crystalline vesicles having size less than 5 microns.

2. A composition according to claim 1, wherein a fatty acyl isethionate product used in a process for making said composition comprises mixtures of 60-95% fatty acyl isethionate and 35-3% free fatty acids.

3. A composition according to claim 1, wherein amount of alkanolamide and/or ≧20 wt. of total amount of fatty acyl isethionate and synthetic cosurfactants of item a and b of claim 1.

4. A composition according to claim 1, additionally comprising 1 to 50% emollient.

5. A composition according to claim 1, wherein the aliphatic hydrocarbon oil is linear hydrocarbon having $C_9$ to $C_{30}$ chain length.

6. A composition according to claim 1, wherein water-soluble and/or dispersible polymer is a polymer selected from the group consisting of starch granule xanthan gum, Carbopol, cross-linked soluble emulsion polymers, cationic guars and mixtures thereof.

* * * * *

UNITED STATES PATENT AND TRADEMARK OFFICE
CERTIFICATE OF CORRECTION

| | | |
|---|---|---|
| PATENT NO. | : 7,659,235 B2 | Page 1 of 1 |
| APPLICATION NO. | : 11/613617 | |
| DATED | : February 9, 2010 | |
| INVENTOR(S) | : Liang Sheng Tsaur, Kavssery Parameswaran Ananthapadmanabhan and Virgilio Barba Villa | |

It is certified that error appears in the above-identified patent and that said Letters Patent is hereby corrected as shown below:

Title Page, Item (54) and at Column 1, lines 1-4, title should read:

-- Stable Liquid Cleansing Compositions Which May Be Prepared Using Broad Selection of Fatty Acyl Isethionate Surfactants --

Signed and Sealed this

Sixth Day of April, 2010

David J. Kappos
*Director of the United States Patent and Trademark Office*

UNITED STATES PATENT AND TRADEMARK OFFICE
Certificate

Patent No. 7,659,235 B2                        Patented: February 9, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Liang Sheng Tsaur, Norwood, NJ (US); Kavssery Parameswaran Ananthapadmanabhan, Woodbury, NJ (US); Virgilio Barba Villa, Emerson, NJ (US); and Rajendra Mohanlol Dave, Newark, NJ (US).

Signed and Sealed this Twenty-ninth Day of April 2014.

*HAROLD PYON*
*Supervisory Patent Examiner*
Art Unit 1761
Technology Center 1700